United States Patent
Su et al.

(10) Patent No.: US 9,169,183 B1
(45) Date of Patent: Oct. 27, 2015

(54) METHOD FOR COPRODUCING ISOBUTENE AND ETBE FROM TERT-BUTANOL MIXTURE

(71) Applicant: CPC Corporation, Taiwan, Taipei (TW)

(72) Inventors: Wei-Bin Su, Taipei (TW); Karl Tze-Tang Chuang, Taipei (TW); Chung-Chen Lai, Taipei (TW); Yung-Sheng Ho, Taipei (TW)

(73) Assignee: CPC CORPORATION, TAIWAN, Taipei (TW)

( * ) Notice: Subject to any disclaimer, the term of this patent is extended or adjusted under 35 U.S.C. 154(b) by 0 days.

(21) Appl. No.: 14/524,754

(22) Filed: Oct. 27, 2014

(51) Int. Cl.
 *C07C 41/09* (2006.01)
 *C07C 1/24* (2006.01)
 *C07C 41/42* (2006.01)

(52) U.S. Cl.
 CPC . *C07C 41/09* (2013.01); *C07C 1/24* (2013.01); *C07C 41/42* (2013.01)

(58) Field of Classification Search
 CPC .................................. C07C 41/09; C07C 1/20
 USPC .......................................... 568/698; 585/639
 See application file for complete search history.

(56) References Cited

U.S. PATENT DOCUMENTS

| | | | |
|---|---|---|---|
| 4,423,271 A | 12/1983 | Obenaus et al. | |
| 5,292,946 A | 3/1994 | Simpson et al. | |
| 5,527,970 A | 6/1996 | Hwan et al. | |
| 5,849,971 A | 12/1998 | Sakuth et al. | |
| 7,825,282 B2 | 11/2010 | Loescher et al. | |

OTHER PUBLICATIONS

Sneesby et al., "ETBE Synthesis via Reactive Distillation. 1. Steady-State Simulation and Design Aspects", Ind. Eng. Chem. Res., 1997, vol. 36, pp. 1855-1869.

Yin et al., "Kinetics of Liquid-Phase Synthesis of Ethyl tert-Butyl Ether from tert-Butyl Alcohol and Ethanol Catalyzed by Ion Exchange Resin and Heteropoly Acid", 1995, International Journal of Chemical Kinetics, vol. 27, pp. 1065-1074.

*Primary Examiner* — Sikarl Witherspoon
(74) *Attorney, Agent, or Firm* — Muncy, Geissler, Olds & Lowe, P.C.

(57) ABSTRACT

This invention describes a method for co-producing isobutene and ethyl tert-butyl ether from tert-butanol mixture in a catalytic distillation column, wherein catalyzing the tert-butanol mixture with the ethanol undergoes dehydration and etherification. The tert-butanol mixture contains absolute ethanol or aqueous ethanol as the antifreeze agent. The isobutene and the ethyl tert-butyl ether withdrawn from the column top are further separated, thus high purity isobutene and ethyl tert-butyl ether for fuel-additive are obtained.

18 Claims, 4 Drawing Sheets

METHOD FOR COPRODUCING ISOBUTENE AND ETBE FROM TERT-BUTANOL MIXTURE

BACKGROUND OF THE INVENTION

1. Field of the Invention

The present invention relates to a process for the co-preparation of isobutene and ethyl tert-butyl ether (ETBE), and in particular to a method for co-producing isobutene and ethyl tert-butyl ether by catalyzing tert-butanol (TBA) mixture with the ethanol undergoes dehydration and etherification.

2. The Prior Arts

Isobutene is the raw material to manufacture alkylate, MTBE/ETBE, diisobutylene, polyisobutene, methacrylic acid, butylated phenols, etc. There are three sources of isobutene: catalytic cracking, steam cracking, and dehydrogenation of butanes. However, in those processes isobutene is always produced as a mixture of C4s isomers. It is costly to produce high purity isobutene from those mixtures due to their close boiling points.

There are currently three important processes for the production of high purity isobutene: (1) the extraction process using a mixture of C4s isomers to separate isobutene, (2) the dehydration of tert-butanol, and (3) the cracking of MTBE. The expected demand for MTBE/ETBE precludes the third route for isobutene production. MTBE/ETBE is more valuable than TBA due to its huge demand as an additive in gasoline fuel. TBA is an important source of isobutene and its derivatives by dehydration of TBA. In addition, the isobutylene and ETBE may be produced from TBA by reaction with ethanol directly into ETBE.

U.S. Pat. No. 5,292,964 discloses a process for preparing alkyl tertiary butyl ether by sequential reaction. For example, TBA and ethanol are reacted in a first reactor and the effluent is charged to the first distillation column, thus a mixture of ethanol and ETBE is obtained from this column top. The ethanol and ETBE mixture is further reacted with isobutylene in a second reactor to form additional quantities of ETBE. Not only excess isobutylene has to be added to increase the ETBE yield, but also, the first distillation column is operated on the condition of ethanol-to-ETBE molar ratio of 1:2 to avoid by-products water which forms an azeotropic behavior in the column. Therefore, the flexibility in operation of the process is limited.

U.S. Pat. No. 5,527,970 discloses a serious of catalysts to enhance TBA conversions and ETBE selectivities. The catalyst may be an acid resin or a pentasil zeolite. However, the obtained TBA conversions and the ETBE selectivities by a continuous flow reactor are limited under the thermodynamic equilibrium reaction. The patent did not disclose the separation of by-product (water) issues.

U.S. Pat. No. 7,825,282 discloses a two-step reaction process to avoid water to form an azeotrope with unreacted ethanol, including dehydrating TBA to form isobutylene, and then reacting isobutylene with ethanol to form ETBE. The process is inefficient, and unable to overcome the transportation and storage problems of TBA.

On the other hand, following patents are focus on the isobutene production via TBA dehydration. U.S. Pat. No. 4,423,271 discloses a method, which uses ion exchange resin as catalyst to dehydrate aqueous TBA in a fixed bed. U.S. Pat. No. 5,811,620 discloses a TBA dehydration method for producing isobutene via a reactive distillation column packed with fluoride-treated catalyst. A similar method is also disclosed in U.S. Pat. No. 5,849,971. However, no ethanol is fed to the column and ETBE cannot be cogenerated with isobutene. In order to manufacture ETBE, an etherification process is required to follow with these TBA dehydration process.

The kinetics of liquid phase synthesis of ETBE from TBA and ethanol catalyzed by ion exchange resin has been proposed by Yin et al., Int. J. Chem. Kinnet., 1995, 27, 1065-1074. In their report, the TBA and ethanol undergo etherification and dehydration simultaneously over Amberlyst 15 such that ETBE and isobutene can be co-produced.

The above methods are not suitable for industrial applications. For example, TBA at high purity is in solid state if its temperature is below 25° C. The transportation for market trade is inconvenient. Also, these processes should be localized around the PO/TBA (propylene oxide/tert-butanol) process or isobutene hydration process to avoid the TBA transportation problem.

SUMMARY OF THE INVENTION

In view of the shortcomings and drawbacks of the prior art, a major objective of the present invention is to provide a method for co-producing isobutene and ETBE from TBA mixture, that catalyzing the TBA mixture with the ethanol in a catalytic distillation column. The dehydration of TBA of the TBA mixture and the etherification of TBA with ethanol are occurred, so as to co-produce isobutene and ETBE.

Another objective of the present invention is to provide a method for co-producing isobutene and ETBE from TBA mixture. The TBA mixture contains absolute ethanol or aqueous ethanol as an antifreeze agent, so as to facilitate transport and trade the TBA mixture in the market.

To achieve the afore-mentioned objective, the present invention provides a method for co-producing isobutene and ETBE from TBA mixture, comprising the following steps: providing a catalytic distillation column, the first catalytic distillation column is distinguished into a rectification zone, a catalytic zone, and a stripping zone from the top down; feeding TBA mixture into the rectification zone of the first catalytic distillation column, wherein the TBA mixture including TBA and absolute ethanol or aqueous ethanol; feeding ethanol into the stripping zone of the first catalytic distillation column to make the total ethanol-to-TBA molar ratio of the first catalytic distillation column is 0.1-2.0; and catalyzing the TBA mixture and the ethanol in the catalytic zone of the first catalytic distillation column to make the dehydration of the TBA of the TBA mixture and the etherification of the TBA with ethanol occur simultaneously, and isobutene and ETBE so that co-produced.

The freezing point of TBA at ambient pressure is about 25.1° C. Its transportation is very inconvenient, especially for shipping for long distance. As TBA is used as raw material, the location for manufacturing isobutene and its derivatives should be close to a PO/TBA plant or isobutene hydration plant. Then the downstream products can be easily distributed to customers. Otherwise, considering market demand and production flexibility, locally produced isobutene should be shipped with pressurized vessel for downstream processing. The isobutene transportation is costly.

The object of the present invention is to effectively lower the freezing point of TBA by mixing it with absolute ethanol or aqueous ethanol as an antifreeze agent, such that TBA can be shipped cheaply anywhere. Due to water and ethanol form an azeotrope, the antifreeze agent component based on the cost considerations is the aqueous ethanol that the ethanol-water weight ratio at atmospheric pressure near the azeotropic is 92/8. This TBA mixture can be directly charged to a catalytic distillation column, wherein is equipped with acid catalyst, e.g. Amberlyst 35, to undergo the etherification of the TBA of the TBA mixture and the dehydration of the TBA, simultaneously. The main products are isobutene and ETBE. Another object of the invention is to co-produce isobutene and ETBE from the mixture of TBA and ethanol.

When the concentration of the aqueous ethanol (the ethanol-water weight ratio is 92/8) in the TBA mixture is higher than 10.7 wt %, the freezing point of TBA mixture is below zero degree C. Since the higher the aqueous ethanol concentration in the TBA mixture the lower is the freezing point, the concentration can be adjusted according to the ambient temperature during shipping of the mixture. The process allows the use of this mixture as received. This is called the first feed point of the catalytic distillation column. Additional ethanol, if required can also be fed to the catalytic distillation column as the second feed. The variable feed concentration results in the flexibility to produce a wide range of isobutene-to-ETBE ratio through this invention.

BRIEF DESCRIPTION OF THE DRAWINGS

The related drawings in connection with the detailed description of the present invention to be made later are described briefly as follows, in which.

DETAILED DESCRIPTION OF THE PREFERRED EMBODIMENT

In order to make the structure and characteristics as well as the effectiveness of the present invention to be further understood and recognized, the detailed description of the present invention is provided as follows along with embodiments and accompanying figures.

Figure 1:
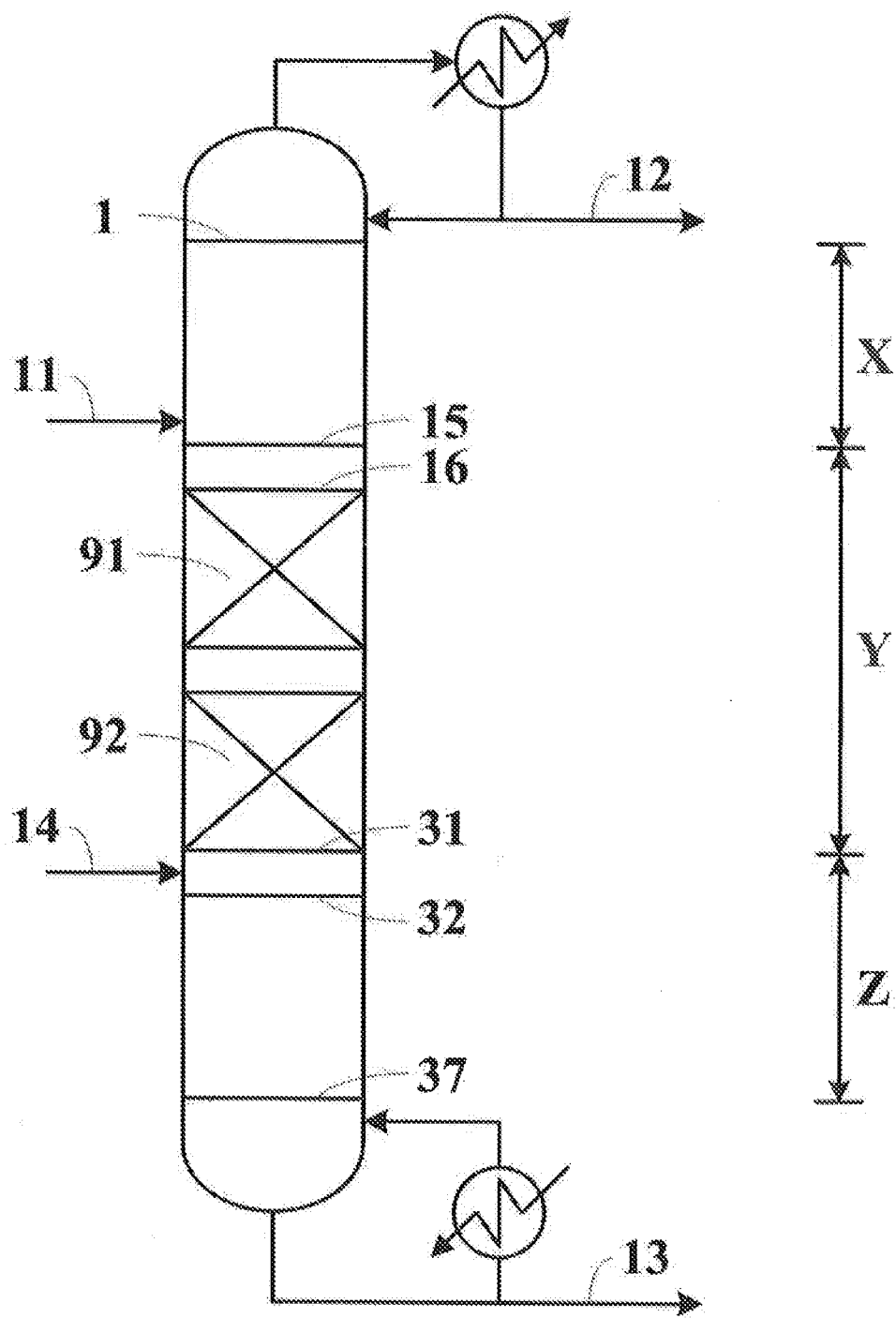
FIG. 1 shows schematic diagram of the first catalytic distillation column for co-producing of ETBE and isobutene.

FIG. 1 is a schematic diagram of the column for co-production of ETBE and isobutene.

The first catalytic distillation (CD) column contains a total of 37 trays, with additional reboiler and a total or partial condenser. The first CD column is divided into three zones. The top zone is a rectification zone X, trays numbered from 1 to 15. Middle zone is a catalytic zone Y with an upper bed 91 and a lower bed 92, trays 16 to 31. The bottom zone is a stripping zone Z, trays 32 to 37. A single-bed catalyst or dual-bed catalysts can be applied to the catalytic zone Y. Moreover, in the dual-bed catalysts, the allowable operating temperature of an upper bed catalyst is lower than a lower bed catalyst. The catalytic zone Y comprises at least a solid acid catalyst, wherein the ion exchange resin with sulfonic acid group is particularly suitable for use. Said ion exchange resin with sulfonic acid group is characterized in having acid capacity more than 2.0 meq/g, e.g. Amberlyst® 15, Amberlyst® 35, Amberlyst® 70, Purolite® CT-275, Purolite® CT-482. Other inorganic catalysts are acceptable and able to be used, e.g. aluminum silicon oxide which treated by fluoride, sulfuric acid, or sulfonic acid; or Y-type zeolite or HZSM-5 zeolite; or any combination thereof.

As shown in FIG. 1, the TBA mixture and additional ethanol are charged to the rectification zone X and stripping zone Z via the lines 11 and 14, respectively. The TBA mixture includes TBA with absolute ethanol or aqueous ethanol, wherein the concentration of the absolute ethanol or the aqueous ethanol is 2-30 wt %, and 5-20 wt % is preferred. In addition, the concentration of ethanol in the aqueous ethanol is more than 80 wt %, wherein the ethanol-water weight ratio close to 92/8 is preferred. The best feed location is above the upper bed 91 for TBA mixture and below the lower bed 92 for absolute ethanol or aqueous ethanol.

In this way, TBA dehydration, TBA and ethanol etherification can occur simultaneously in the catalytic zone Y. Light products, isobutene and ETBE, will be withdrawn from the top of the first CD column, the line 12. Heavy compounds, water and excess ethanol, will be withdrawn from the bottom, the line 13. By blending the fresh TBA with the required absolute ethanol or aqueous ethanol, or supplying fresh ethanol as an additional feed, this column design allows high flexibility to produce desirable isobutene-to-ETBE ratio. This is because the product of isobutene-to-ETBE ratio is partly dependent on the total ethanol that is charged to the first CD column.

Figure 2:
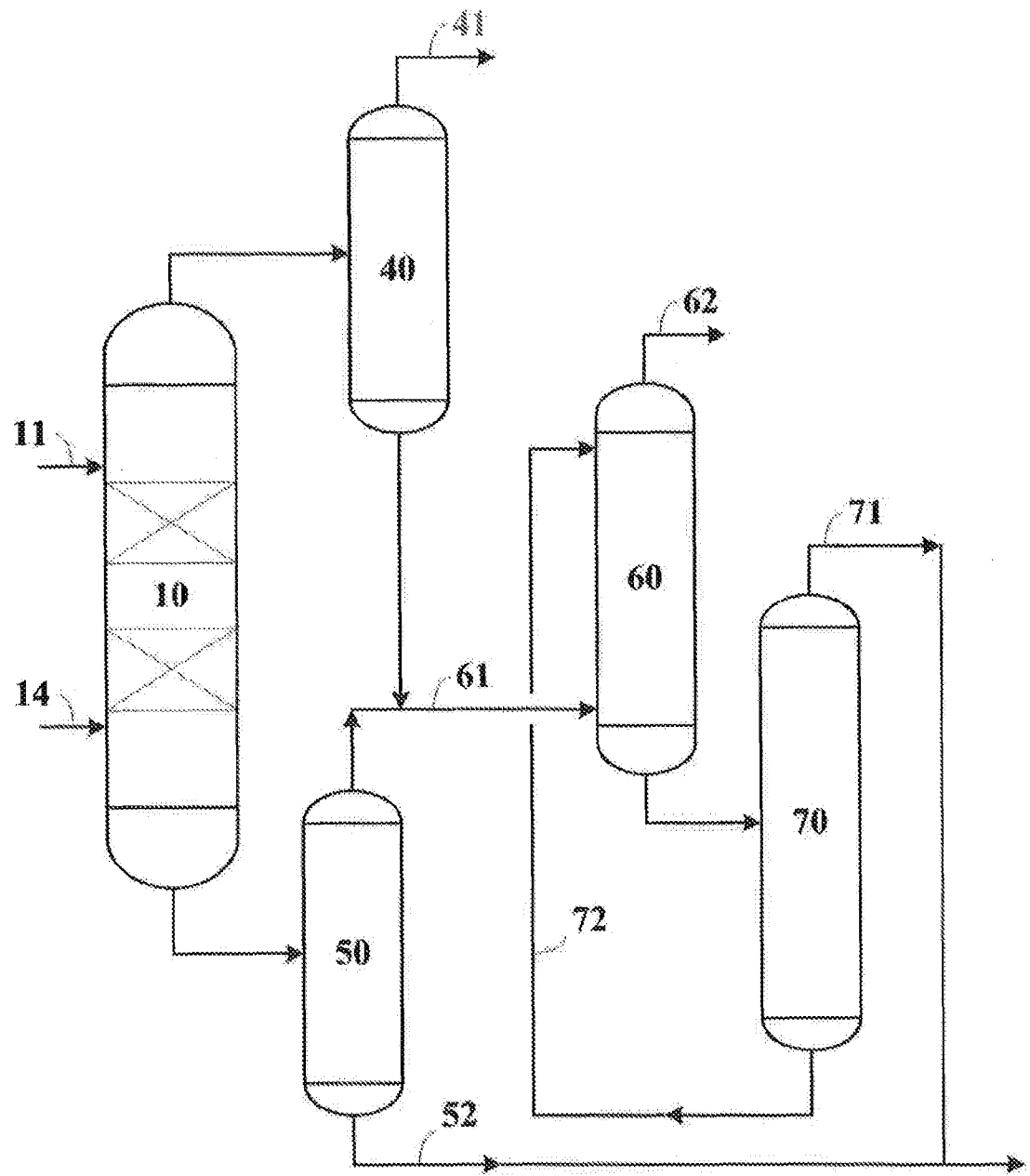
FIG. 2 shows a structural schematic diagram according to an embodiment co-producing isobutene and ETBE from TBA mixture.

FIG. 2 shows a structural schematic diagram according to an embodiment co-producing isobutene and ETBE from TBA mixture, where the columns connected by lines which made by pipes.

The TBA mixture fed from line 11 is charged to the first CD column 10. For high ETBE yield, the supplied ethanol is fed through the line 14 to the first CD column 10. The effluent from the top of the first CD column 10 contains mostly isobutene and ETBE. This effluent is fed to the isobutene column 40. The isobutene column 40 distills an isobutene and ETBE mixture to separate an isobutene primary product that exits at the top of the isobutene column 40 via the line 41. The effluent from the bottom of the isobutene column 40 contains a mixture of ETBE and ethanol. It is fed to the extractive distillation column 60 via the line 61. The effluent from the bottom of the first CD column 10 contains mostly by-products, water and unreacted ethanol. This effluent is fed to the waste concentrating column 50. The waste concentrating column 50 distills ethanol and water mixture to a high purify water that is sent to a wastewater treatment plant via the line 52. An azeotrope with water coming from the top of the waste concentrating column 50 is fed to the extractive distillation column 60 via the line 61. The stream including the ethanol and water mixture, ETBE, and unreacted TBA from the line 61 is fed to the bottom of the extractive distillation column 60. The extraction solvent, ethylene glycol, is fed in the top of the extractive distillation column 60 via the line 72. The ethylene glycol and water mixture is withdrawn from the bottom of the extractive distillation column 60. The ETBE, ethanol and TBA mixture is withdrawn from the top of the extractive distillation column 60 via the line 62 to be employed as oxygenated fuel-additives and incorporated directly into a gasoline pool. The water and ethylene glycol mixture is fed to the extraction solvent recovery column 70. The extraction solvent recovery column 70 distills the water and ethylene glycol mixture into water and ethylene glycol. The water coming from the top of the extraction solvent recovery column 70 is sent to a wastewater treatment plant via the line 71. The ethylene glycol coming from the bottom of the extraction solvent recovery column 70 is recycled to the extractive distillation column 60 via the line 72.

Figure 3:
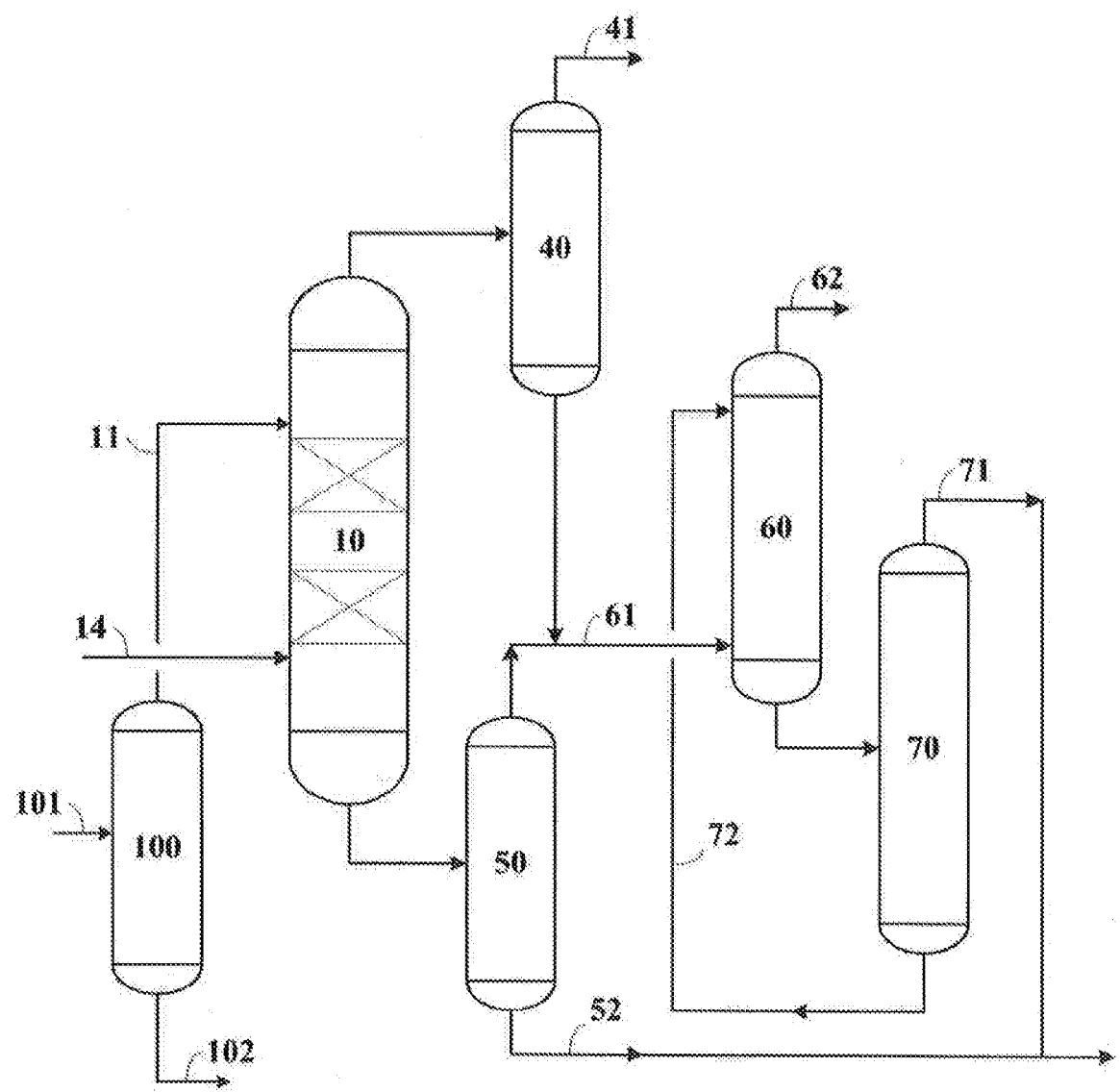
FIG. 3 shows a structural schematic diagram according to another embodiment co-producing isobutene and ETBE from TBA mixture.

FIG. 3 shows another embodiment co-producing isobutene and ETBE from TBA mixture, which contaminates with butanol isomers.

The impurities in crude TBA coming from the PO/TBA process are mainly isobutanol and 2-butanol. Because the boiling point of TBA is the lowest among butanol isomers, the TBA mixture priorly charged to the first CD column 10 can be fed through the line 101 and distilled in the de-butanol column 100 to remove the heavier isomers from the bottom of the column via the line 102. Thus, the impact of butanol isomers on the this invention can be minimized and the first CD column 10, isobutene column 40, waste concentrating column 50, extractive distillation column 60 and extraction solvent recovery column 70 can work well.

Figure 4:
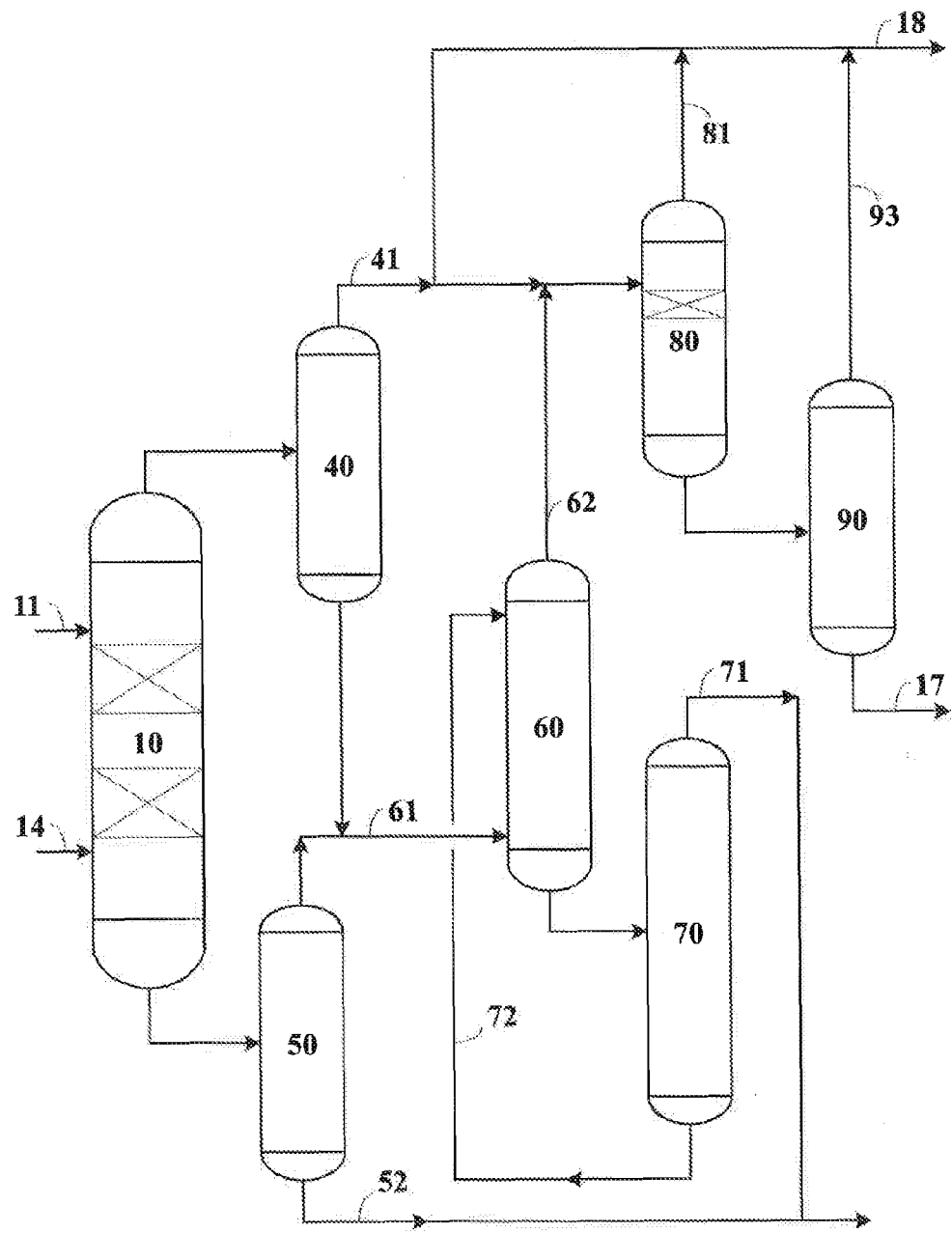
FIG. 4 shows a structural schematic diagram according to still another embodiment co-producing isobutene and ETBE from TBA mixture.

FIG. 4 shows another embodiment co-producing isobutene and ETBE from TBA mixture, wherein the ETBE, ethanol and TBA mixture coming from the top of the extractive distillation column 60 via the line 62 is further converted into high purity ETBE so as to trade in the market.

A stream of the isobutene primary product via the line 41 and a stream of the ethanol and ETBE mixture via the line 62 are mixed and fed into the second CD column 80. The isobutene-to-ethanol molar ratio of the mixture is more than 1.1 such that the ethanol can be mostly converted to ETBE by catalytic distillation in the second CD column 80. ETBE is withdrawn from the bottom of the second CD column 80 and fed to the de-isobutene column 90. The excess isobutene from the top of the second CD column 80 is withdrawn via the line 81. The de-isobutene column 90 separates ETBE and removes residual isobutene by distillation. The removed residual isobutene is mixed with the isobutene primary product via the line 93 and finally the isobutene product is sent to storage tank via line 18. The high purity ETBE is obtained from the bottom of the de-isobutene column 90 via the line 17.

The following examples show the effects of the operating variables on TBA conversion and isobutene selectivity, which are simulated with a commercial software, ASPEN PLUS. The model input parameters are summaried as follows.

To the best of our knowledge, the quantity corresponding to the TBA feed rate to the first CD column 10 in FIG. 2 is about 12.5 ton/hr. Including one reboiler and one condenser, there are 37 theoretical plates in the first CD column model, numbered from top to bottom. The catalytic zone is located between plates 16 and 31. The TBA or TBA mixture is fed above plate 16 at 100° C. The supplied ethanol is fed below plate 32 at 110° C. The catalyst volume per tray in the catalytic zone is assumed to be 12% of tray spacing. The diameter of the first CD column is dependent on the operating parameters, such as column pressure, ethanol-to-TBA molar ratio, reflux ratio, distillate-to-feed ratio. The default sieve tray sizing equation in ASPEN PLUS is selected for the design calculations. The rate equations for calculating reaction rates are adopted from the work of Yin et al. (Kinetics of Liquid Phase Synthesis of Ethyl tert-Butyl Ether from tert-Butyl Alcohol and Ethanol Catalyzed by Ion Exchange Resin, International Journal of Chemical Kinetics, 27 (10), 1065-1074, 1995.). The default UNIQUAC method in the ASPEN PLUS software is used to compute vapor-liquid equilibrium compositions. Coupling with operating parameters, the first CD column model can be solved to obtain the information on isobutene and ETBE product streams. In the present invention, the operating parameters of the first CD column defined as: column pressure is set at 2-7 kg/cm$^2$, preferred range is 4-6 kg/cm$^2$; temperature is between 20-160° C., preferably 40-145° C.; ethanol-to-TBA molar ratio, reflux ratio, and distillated-to-feed mass ratio are 0.1-2.0, 1-20, 0.3-0.9, respectively, preferably 0.15-1.5, 2-10, and 0.5-0.85.

TBA conversion and isobutene selectivity are defined as following equations.

$$X_{TBA}=(1-F_{out}/F_{in}|_{TBA})\times 100\%$$

$$S_{IB}=(F_{IB}/(F_{IB}+F_{ETBE}))\times 100\%$$

In above equations, the F is molar flow, in/out is the inlet/outlet of the first CD column and TBA/IB/ETBE is TBA/isobutene/ETBE.

Ethylene glycol is used as an extraction solvent in the extractive distillation column to modify the relative volatility of ETBE, ethanol, TBA and etc. with water. ETBE, ethanol, TBA and etc. are distilled and extracted from the top of the extractive distillation column. The water is withdrawn accompanying the ethylene glycol from the bottom of the extractive distillation column.

For the second CD column model, the rate equations for calculating ETBE synthesis rates are adopted from the work of Sneesby et al. (ETBE Synthesis via Reactive Distillation. 1. Steady-State Simulation and Design Aspects, Ind. Eng. Chem. Res., 36(5), 1855-1869, 1997). The default UNIQUAC method in the ASPEN PLUS software is used to compute vapor-liquid equilibrium compositions. Coupling with operating parameters, the second CD column model can be solved to obtain the information on the ETBE production.

Example 1

The solid state TBA (Merck reagent grade, >99.5%) is melted in a water bath at constant temperature of 45° C. 126.1 gram of TBA is weighted and put into a 500 mL of erlenmeyer flask and 6.3 gram of aqueous ethanol (the ethanol-water weight ratio is 92/8 wt %) is added to the TBA. The TBA mixture solutions with 5 wt %, 8 wt %, 10 wt % and 15 wt % of aqueous ethanol concentration respectively are obtained. A rubber stopper attached to an alcohol thermometer is used to plug the flask. The flask is moved to a refrigerator circulated with ethanol and gradually cooled down from 20° C. The flask is shaked from time to time. The freezing temperature is decreased 0.5° C. for each time after temperature reaches equilibrium between coolant and the solution. Carefully observe the thermometer and if crystal is formed. Record the crystallizing-out temperature. Repeat one time to measure the cloud point of the TBA mixture. The cloud points of TBA mixed with 5 wt %, 8 wt %, 10 wt % and 15 wt % of aqueous ethanol are measured with the above mentioned procedure. Results are summarized in Table 1. It can be seen that the aqueous ethanol can be as an antifreeze agent for TBA.

TABLE 1

| aqueous ethanol, wt % (ethanol-water weight ratio is 92/8 wt %) | 5 | | 8 | | 10 | | 15 | |
|---|---|---|---|---|---|---|---|---|
| Test no. | 1 | 2 | 1 | 2 | 1 | 2 | 1 | 2 |
| Cloud point, ° C. | 8 | 8 | 2.4 | 1.6 | −2 | −1 | −17 | −19 |

Example 2

This example is a base case for exploring the effects of operating parameters on isobutene selectivity.

This example demonstrates a co-production process for isobutene and ETBE, where the TBA mixture is used as feed and the supplied fresh absolute ethanol is used as second feed by 0.562 ton/hr. The TBA concentration in the mixture comprising of TBA and 92% aqueous ethanol is 89.3 wt %. The total ethanol-to-TBA molar ratio in the first CD column is 0.25. Other unit parameters of the first CD column are given below. Column pressure is set at 4.5 kg/cm$^2$ and total condenser is subcooled at 43.2° C. As reflux ratio and distillate to feed mass ratio are 3.4 and 0.76, the column size can be determined by these column parameters. Then, the calculated catalyst volume per tray is 0.197 m$^3$. The calculated reaction temperature at the catalytic zone is 113.1-123.0° C. TBA conversion and isobutene selectivity are 99.2% and 89.7%, respectively.

Example 3

This example demonstrates the effect of low ethanol to TBA molar ratio on isobutene selectivity.

Comparing with Example 2, no supplied fresh absolute ethanol or aqueous ethanol to the first CD column are required. The total ethanol-to-TBA molar ratio in the first CD column is 0.178. Other unit parameters of the first CD column are given below. Column pressure is set at 4.5 kg/cm$^2$ and total condenser is subcooled at 41.6° C. As reflux ratio and distillate to feed mass ratio are 3.0 and 0.75, the column size can be determined by these column parameters. Then, the calculated catalyst volume per tray is 0.178 m$^3$. The calculated reaction temperature at the catalytic zone is 110.0-123.2° C. TBA conversion and isobutene selectivity are 99.2% and 93.4%, respectively.

Example 4

This example demonstrates the effect of high ethanol to TBA molar ratio on isobutene selectivity.

Comparing with Example 2, the 85% TBA mixture is used as feed, and the supplied fresh absolute ethanol is used as second feed by 5.74 ton/hr. The total ethanol-to-TBA molar ratio in the first CD column is 1.0. Other unit parameters of the first CD column are given below. Column pressure is set at 4.5 kg/cm$^2$ and total condenser is subcooled at 45.1° C. As reflux ratio and distillate to feed mass ratio are 4.2 and 0.575, the column size can be determined by these column parameters. Then, the calculated catalyst volume per tray is 0.224 m$^3$. The calculated reaction temperature at the catalytic zone is 115.7-122.4° C. TBA conversion and isobutene selectivity are 99.2% and 85.5%, respectively.

By comparing Examples 2-4, TBA conversion more than 99% can prove that the effect of higher ethanol to TBA molar ratio to improve isobutene selectivity is limited.

Example 5

This example demonstrates the effect of lower column pressure on isobutene selectivity.

Comparing with Example 2, the column pressure of the first CD column is set at 2.5 kg/cm$^2$. Other unit parameters of the first CD column are given below. The total ethanol-to-TBA molar ratio in the first CD column is 0.25. The total condenser is subcooled at 23.9° C. As reflux ratio and distillate to feed mass ratio are 6.0 and 0.765, the column size can be determined by these column parameters. Then, the calculated catalyst volume per tray is 0.29 m$^3$. The calculated reaction temperature at the catalytic zone is 98.2-105.1° C. TBA conversion and isobutene selectivity are 97.7% and 86.0%, respectively.

Example 6

This example demonstrates the effect of higher column pressure on isobutene selectivity.

Comparing with Example 2, the column pressure of the first CD column increases to 6.5 kg/cm$^2$. Other unit parameters of the first CD column are given below. The total ethanol-to-TBA molar ratio in the first CD column is 0.25. The total condenser is subcooled at 56.7° C. As reflux ratio and distillate to feed mass ratio are 2.8 and 0.75, the column size can be determined by these column parameters. Then, the calculated catalyst volume per tray is 0.165 m$^3$. The calculated reaction temperature at the catalytic zone is 124.4-136.1° C. TBA conversion and isobutene selectivity are 99.4% and 92.0%, respectively.

By comparing Examples 2, 5 and 6, TBA conversion more than 98% can prove that the effect of higher column pressure to improve isobutene selectivity is limited. In other words, higher column pressure fails to lower ETBE yield.

Table 2 summarizes the operating parameters of the first CD column for Examples 2-6, and their effects on TBA conversion and isobutene selectivity. Table 3 is the product data of the first CD column for Examples 2-6.

TABLE 2

Operating parameters: $N_{total}$ = 37, $N_{TBA}$ = 15, $N_{EtOH}$ = 32, $N_{cat}$ = 16-31, $T_{TBA}$ = 100° C., $T_{EtOH}$ = 110° C.

| | Ex2 | Ex3 | Ex4 | Ex5 | Ex6 |
|---|---|---|---|---|---|
| Pressure, kg/cm$^2$ | 4.5 | 4.5 | 4.5 | 2.5 | 6.5 |
| EtOH/TBA molar ratio | 0.25 | 0.178 | 1.0 | 0.25 | 0.25 |
| $T_{condenser}$, ° C. | 43.2 | 41.6 | 44.5 | 23.9 | 56.7 |
| Reflux ratio | 3.4 | 3 | 4.2 | 6.0 | 2.8 |
| Distillate to feed mass ratio | 0.76 | 0.75 | 0.575 | 0.765 | 0.75 |
| Cat. vol. per tray, m$^3$ | 0.197 | 0.178 | 0.224 | 0.290 | 0.165 |
| TBA conversion, % | 99.2 | 99.2 | 99.2 | 97.7 | 99.4 |
| Isobutene selectivity, % | 89.7 | 93.4 | 85.5 | 86.0 | 92.0 |

TABLE 3

Product data of the first CD column

| | stream no. | flow ton/hr | weight fraction | | | | |
|---|---|---|---|---|---|---|---|
| | | | iC$_4$- | ETBE | EtOH | TBA | H$_2$O |
| Ex2 | 12 | 11.7 | 0.7612 | 0.1586 | 0.0571 | 0.0078 | 0.0152 |
| | 13 | 3.49 | 0 | 0 | 0.1483 | 0.003 | 0.8487 |
| Ex3 | 12 | 10.5 | 0.8352 | 0.1073 | 0.0376 | 0.0077 | 0.0122 |
| | 13 | 3.5 | 0 | 0 | 0.1363 | 0.0049 | 0.8588 |
| Ex4 | 12 | 11.76 | 0.6825 | 0.2107 | 0.0886 | 0.003 | 0.0152 |
| | 13 | 8.69 | 0 | 0 | 0.6457 | 0.0078 | 0.3464 |
| Ex5 | 12 | 11.14 | 0.7137 | 0.2116 | 0.0515 | 0.0091 | 0.0141 |
| | 13 | 3.42 | 0 | 0 | 0.0892 | 0.0542 | 0.8565 |
| Ex6 | 12 | 10.92 | 0.7929 | 0.1247 | 0.0609 | 0.0065 | 0.015 |
| | 13 | 3.64 | 0 | 0 | 0.1822 | 0.0002 | 0.8176 |

Example 7

This example demonstrates a co-production process for isobutene and ETBE, where the TBA mixture is used as feed and the supplied fresh aqueous ethanol with 92 wt % ethanol concentration is used as second feed. Considering the transportation feasibility, the aqueous ethanol concentration in the mixture is 10.7 wt %. The freezing point of the mixture is below 0° C. same as that in Example 1. The TBA mixture is fed above plate number 15 at 100° C. via line 11. The supplied fresh aqueous ethanol is fed above plate number 32 by 0.611 ton/hr at 110° C. via line 14. The total ethanol-to-TBA molar ratio of the first CD column is 0.25. Column pressure is set at 4.5 kg/cm$^2$ and total condenser is subcooled at 42.9° C. As reflux ratio and distillate to feed mass ratio are 3.4 and 0.75, the column size can be determined by these column parameters. Then, the calculated catalyst volume per tray is 0.195 m³. The calculated reaction temperature at the catalytic zone is 112.6-123.0° C. TBA conversion and isobutene selectivity are 99.3% and 90.5%, respectively.

Other unit parameters are given below. Isobutene column pressure is set at 5.0 kg/cm² and total condenser is subcooled at 42.0° C. Theoretical plates, feed location, reflux ratio and distillate to feed mass ratio in this column model are 13, 7, 3.0 and 0.775, respectively, and further comprising a reboiler and a condenser. Waste concentrating column pressure is set at 1.1 kg/cm² and total condenser is subcooled at 80.0° C. Theoretical plates, feed location, reflux ratio and distillate to feed mass ratio in this column model are 33, 17, 5.0 and 0.189, respectively, and further comprising a reboiler and a condenser. The ethylene glycol-to-water molar ratio of the extractive distillation column is 5.82. Column pressure is 1.05 kg/cm² and total condenser is subcooled at 65.6° C. Theoretical plates, azeotrope with water feed location, ethylene glycol feed location, reflux ratio and distillate to feed mass ratio in this column model are 38, 5, 34, 1.5 and 0.394, respectively, and further comprising a reboiler and a condenser. Extraction solvent recovery column pressure is set at 0.272 kg/cm² and total condenser is subcooled at 66.4° C. Theoretical plates, feed location, reflux ratio and distillate to feed mass ratio in this column model are 13, 7, 5.0 and 0.044, respectively. Table 4 shows the modeling results for the streams as shown in FIG. 2.

TABLE 4 stream data for Example 7

| Stream number | 11 | 14 | 41 | 62 | 52 | 71 | 72 |
|---|---|---|---|---|---|---|---|
| ton/hr | 14.0 | 0.611 | 8.49 | 2.95 | 2.96 | 0.2 | 4.34 |
| wt% | | | | | | | |
| Isobutene | 0 | 0 | 99.9 | 0.31 | 0 | 0 | 0 |
| ETBE | 0 | 0 | 0 | 55.1 | 0 | 0 | 0 |
| Ethanol | 9.86 | 92.0 | 0.01 | 40.8 | 0 | 0 | 0 |
| TBA | 89.3 | 0 | 0 | 3.14 | 0 | 0 | 0 |
| Water | 0.86 | 8.0 | 0.06 | 0.57 | 100 | 100 | 0 |
| Ethylene glycol | 0 | 0 | 0 | 0 | 0 | 0 | 100 |

Example 8

This example demonstrates a co-production process for isobutene and ETBE, where the TBA mixture is used as feed and no ethanol was supplied. Considering the transportation feasibility, the aqueous ethanol concentration in the TBA mixture is 10.7 wt %. The freezing point of the mixture is below 0° C. same as that in Example 1. The TBA mixture is fed above plate number 15 at 100° C. via line 11. The total ethanol-to-TBA molar ratio of the first CD column is 0.178. Column pressure is set at 4.5 kg/cm² and total condenser is subcooled at 41.6° C. As reflux ratio and distillate to feed mass ratio are 3.0 and 0.75, the column size can be determined by these column parameters. Then, the calculated catalyst volume per tray is 0.178 m³. The calculated reaction temperature at the catalytic zone is 110.0-123.2° C. TBA conversion and isobutene selectivity are 99.2% and 93.4%, respectively.

Other unit parameters are given below. Isobutene column pressure is set at 5.0 kg/cm² and total condenser is subcooled at 42.0° C. Theoretical plates, feed location, reflux ratio and distillate to feed mass ratio in this column model are 13, 7, 3.0 and 0.835, respectively, and further comprising a reboiler and a condenser. Waste concentrating column pressure is set at 1.1 kg/cm² and total condenser is subcooled at 80.0° C. Theoretical plates, feed location, reflux ratio and distillate to feed mass ratio in this column model are 33, 17, 5.0 and 0.154, respectively, and further comprising a reboiler and a condenser. The ethylene glycol-to-water molar ratio of the extractive distillation column is 7.5. Column pressure is 1.05 kg/cm² and total condenser is subcooled at 65.4° C. Theoretical plates, azeotrope with water feed location, ethylene glycol feed location, reflux ratio and distillate to feed mass ratio in this column model are 38, 5, 34, 1.5 and 0.32, respectively, and further comprising a reboiler and a condenser. Extraction solvent recovery column pressure is set at 0.272 kg/cm² and total condenser is subcooled at 66.4° C. Theoretical plates, feed location, reflux ratio and distillate to feed mass ratio in this column model are 13, 7, 5.0 and 0.034, respectively. Table 5 shows the modeling results for the streams as shown in FIG. 2.

TABLE 5 stream data for Example 8

| Stream number | 11 | 14 | 41 | 62 | 52 | 71 | 72 |
|---|---|---|---|---|---|---|---|
| ton/hr | 14.0 | 0 | 8.77 | 2.12 | 2.96 | 0.15 | 4.34 |
| wt% | | | | | | | |
| Isobutene | 0 | 0 | 99.9 | 0.38 | 0 | 0 | 0 |
| ETBE | 0 | 0 | 0 | 53.2 | 0 | 0 | 0 |
| Ethanol | 9.86 | 0 | 0.01 | 41.2 | 0 | 0 | 0 |
| TBA | 89.3 | 0 | 0 | 4.64 | 0 | 0 | 0 |
| Water | 0.86 | 0 | 0.06 | 0.65 | 100 | 99.98 | 0 |
| Ethylene glycol | 0 | 0 | 0 | 0 | 0 | 0.02 | 100 |

Example 9

This example demonstrates a co-production process for isobutene and ETBE, where the TBA mixture contaminated with isobutanol, 2-butanol and water is used as feed and no supplied fresh ethanol. Before mixing with ethanol, the crude TBA (94.5 wt %) coming from the PO/TBA process could contain 1.1% water and 4.4% butanol isomers. To the best of our knowledge, the impurities are mainly water, isobutanol, 2-butanol and 1-butanol. In this example, 4.4% butanol isomers are divided into 2.2% isobutanol and 2.2% 2-butanol. The aqueous ethanol concentration in the TBA mixture is maintained at 11.2 wt % almost as same as in Example 8.

The de-butanol column parameters are given below. Column pressure is set at 0.68 kg/cm² and total condenser is cooled at saturated temperature (71.2° C.). Theoretical plates, feed location, reflux ratio and distillate to feed mass ratio in this column model are 33, 17, 1.5 and 0.961, respectively, and further comprising a reboiler and a condenser. Simulation results show that anhydrous mixture of isobutanol and 2-butanol can be removed from the bottom effluent and water together with TBA and ethanol will go through the top of the column. The anhydrous butanol mixture can be further separated to high purity chemicals or directly used as fuel additives.

Then, the top effluent of the de-butanol column is fed above plate number 15 of the first CD column at 71.6° C. via line 11. The ethanol-to-TBA molar ratio of the first CD column is 0.178. Column pressure is set at 4.5 kg/cm² and total condenser is subcooled at 41.9° C. Once reflux ratio (3.0) and distillate to feed mass ratio (0.75) are selected, the column size can be determined. Then, the calculated catalyst volume per tray is 0.181 m. The calculated reaction temperature at the catalytic zone is 111.2-123.3° C. TBA conversion and isobutene selectivity are 99.3% and 92.7%, respectively. Table 6 shows the modeling parameters and results.

TABLE 6 simulation parameters and results for Examples 8-9

| | Ex8 | Ex9 |
|---|---|---|
| Pressure, kg/cm$^2$ | 4.5 | 4.5 |
| EtOH/TBA molar ratio | 0.178 | 0.178 |
| $T_{condenser}$, ° C. | 41.6 | 41.9 |
| Reflux ratio | 3 | 3 |
| Distillate to feed mass ratio | 0.75 | 0.75 |
| Cat. vol. per tray, m$^3$ | 0.178 | 0.181 |
| TBA conversion, % | 99.2 | 99.3 |
| Isobutene selectivity, % | 93.4 | 92.7 |

Example 10

Comparing with Example 9, this example demonstrates a co-production process for isobutene and ETBE through the first CD column and the second CD column, where the TBA mixture is used as feed and no supplied fresh ethanol. Considering the transportation feasibility, the aqueous ethanol concentration in the TBA mixture is 10.7 wt %. The freezing point of the mixture is below 0° C. same as that in Example 1. The TBA mixture is fed above plate number 15 at 100° C. via line 11. The total ethanol-to-TBA molar ratio of the first CD column is 0.178. Column pressure is set at 4.5 kg/cm$^2$ and total condenser is subcooled at 41.5° C. As reflux ratio and distillate to feed mass ratio are 3.6 and 0.75, the column size can be determined by these column parameters. Then, the calculated catalyst volume per tray is 0.191 m$^3$. The calculated reaction temperature at the catalytic zone is 110.9-123.0° C. TBA conversion and isobutene selectivity are 99.6% and 93.8%, respectively.

Other unit parameters are given below. Isobutene column pressure is set at 5.0 kg/cm$^2$ and total condenser is subcooled at 41.9° C. Theoretical plates, feed location, reflux ratio and distillate to feed mass ratio in this column model are 13, 7, 3.0 and 0.842, respectively, and further comprising a reboiler and a condenser. Waste concentrating column pressure is set at 1.1 kg/cm$^2$ and total condenser is subcooled at 80.0° C. Theoretical plates, feed location, reflux ratio and distillate to feed mass ratio in this column model are 33, 17, 5.0 and 0.145, respectively, and further comprising a reboiler and a condenser. The ethylene glycol-to-water molar ratio of the extractive distillation column is 8.43. Column pressure is 1.05 kg/cm$^2$ and total condenser is subcooled at 64.8° C. Theoretical plates, azeotrope with water feed location, ethylene glycol feed location, reflux ratio and distillate to feed mass ratio in this column model are 38, 5, 34, 1.5 and 0.312, respectively, and further comprising a reboiler and a condenser. Extraction solvent recovery column pressure is set at 0.272 kg/cm$^2$ and total condenser is subcooled at 66.4° C. Theoretical plates, feed location, reflux ratio and distillate to feed mass ratio in this column model are 13, 7, 5.0 and 0.03, respectively.

Second CD column pressure is set at 5.5 kg/cm$^2$ and total condenser is subcooled at 45.6° C. The confluence mixture is fed above plate number 5 of the second CD column at 60° C. The catalytic zone is configured between plates 6-8. The isobutene-to-ethanol molar ratio of the second CD column is 1.98. As reflux ratio and distillate to feed mass ratio in this column model are 4.0 and 0.26, the column size can be determined by these column parameters. Then, the calculated catalyst volume per tray is 0.041 m$^3$. The calculated reaction temperature at the catalytic zone is 52.9-61.1° C. The ethanol conversion is 93.0%. De-isobutene column pressure is set at 7.0 kg/cm$^2$ and total condenser is subcooled at 55.2° C. Theoretical plates, feed location, reflux ratio and distillate to feed mass ratio in this column model are 18, 9, 7.0 and 0.018, respectively, and further comprising a reboiler and a condenser. After the secondary catalytic distilling reaction in the second CD column, the yield of the final product, isobutene and ETBE with respect to TBA are 82.6% and 16.9%, respectively.

TABLE 7 stream data for Example 10

| Stream number | 11 | 14 | 41 | 62 | 72 | 10 | 17 |
|---|---|---|---|---|---|---|---|
| ton/hr | 14.0 | 0 | 8.84 | 2.03 | 4.34 | 7.82 | 3.05 |
| wt% | | | | | | | |
| Isobutene | 0 | 0 | 99.94 | 0.47 | 0 | 99.92 | 0.25 |
| ETBE | 0 | 0 | 0 | 52.1 | 0 | 0 | 95.7 |
| Ethanol | 9.86 | 0 | 0.01 | 44.4 | 0 | 0.03 | 2.01 |
| TBA | 89.3 | 0 | 0 | 2.31 | 0 | 0 | 1.54 |
| Water | 0.86 | 0 | 0.05 | 0.72 | 0 | 0.05 | 0.51 |
| Ethylene glycol | 0 | 0 | 0 | 0 | 100 | 0 | 0 |

Accordingly, the present invention conforms to the legal requirements owing to its novelty, nonobviousness, and utility. However, the foregoing description is only embodiments of the present invention, not used to limit the scope and range of the present invention. Those equivalent changes or modifications made according to the shape, structure, feature, or spirit described in the claims of the present invention is included in the appended claims of the present invention.

What is claimed is:

1. A method for coproducing isobutene and ethyl tert-butyl ether (ETBE) from tert-butanol (TBA) mixture, wherein said method comprising steps:
   providing a catalytic distillation column, the first catalytic distillation column is distinguished into a rectification zone, a catalytic zone, and a stripping zone from the top down;
   feeding TBA mixture into the rectification zone of the first catalytic distillation column, wherein the TBA mixture including TBA and absolute ethanol or aqueous ethanol;
   feeding ethanol into the stripping zone of the first catalytic distillation column to make the total ethanol-to-TBA molar ratio of the first catalytic distillation column is 0.1-2.0; and
   catalyzing the TBA mixture and the ethanol in the catalytic zone of the first catalytic distillation column to make the dehydration of the TBA of the TBA mixture and the etherification of the TBA with ethanol occur simultaneously, and isobutene and ETBE so that co-produced,
   wherein the concentration of the absolute ethanol or the aqueous ethanol in the TBA mixture is 2-30 wt %, and
   wherein the concentration of ethanol in the aqueous ethanol is more than 80 wt %.

2. The method as claimed in claim 1, wherein the concentration of the absolute ethanol or the aqueous ethanol in the TBA mixture is 5-20 wt %.

3. The method as claimed in claim 1, wherein the ethanol-water weight ratio in the aqueous ethanol is 92/8.

4. The method as claimed in claim 1, wherein the catalytic zone has at least a catalyst, where the catalyst is an ion exchange resin with sulfonic acid group, the ion exchange resin with sulfonic acid group having acid capacity more than 2.0 meq/g.

5. The method as claimed in claim 4, wherein the catalytic zone comprises a single-bed catalyst or dual-bed catalysts, where in the dual-bed catalysts, the allowable operating temperature of an upper bed catalyst is lower than the allowable operating temperature of a lower bed catalyst.

6. The method as claimed in claim 1, wherein the column pressure of the first catalytic distillation column is 2-7 kg/cm$^2$, the temperature profile of the first catalytic distillation column is 20-160° C., the reflux ratio in the first catalytic distillation column is 1-20, and the distillated-to-feed mass ratio in the first catalytic distillation column is 0.3-0.9.

7. The method as claimed in claim 1, wherein after the step of catalyzing the TBA mixture and the ethanol in the catalytic zone of the first catalytic distillation column, further comprises step:
purifying products of the first catalytic distillation to obtain the isobutene and the ETBE through distillation, extractive-distillation, and second catalytic distillation.

8. The method as claimed in claim 7, wherein in the step of purifying the isobutene and the ETBE, further comprises the steps of:
feeding the top products of the first catalytic distillation column into an isobutene column, wherein the isobutene column distills isobutene and ETBE mixture to separate an isobutene primary product;
feeding the bottom products of the first catalytic distillation column into a waste concentrating column, wherein the waste concentrating column distills ethanol and water mixture to purify water; and
feeding the products of the first catalytic distillation column into an extractive distillation column, wherein the extractive distillation column removes water from ethanol, ETBE and water mixture by extractive distillation to obtain a fuel-grade ethanol and ETBE mixture.

9. The method as claimed in claim 8, wherein the first catalytic distillation column further connects with the isobutene column to purify isobutene, and connects with the waste concentrating column to purify water, wherein the isobutene column and the waste concentrating column further connect with the extractive distillation column to feed the ethanol, isobutene and water mixture into the bottom of the extractive distillation column and extract the ethanol and ETBE mixture from the top of the extractive distillation column.

10. The method as claimed in claim 9, wherein the top of the extractive distillation column further feeds an extraction solvent from an extraction solvent recovery column and connects with the extraction solvent recovery column, and the bottom of the extractive distillation column further feeds the extraction solvent and water to the extraction solvent recovery column.

11. The method as claimed in claim 10, wherein the extraction solvent recovery column further distills the extraction solvent and the water to separate the water from the top and the extraction solvent from the bottom of the extraction solvent recovery column respectively, wherein the extraction solvent recycles to the extractive distillation column.

12. The method as claimed in claim 10, wherein the extraction solvent is ethylene glycol.

13. The method as claimed in claim 8, further comprises mixing the isobutene primary product and the ethanol and ETBE mixture into a mixture and feeding into a second catalytic distillation column, where the second catalytic distillation column converts ethanol to ETBE by catalytic distillation, wherein the isobutene-to-ethanol molar ratio of the mixture is more than 1.1.

14. The method as claimed in claim 13, wherein the excess isobutene from the top of the second catalytic distillation column is blended into the isobutene primary product, the bottom of the second catalytic distillation column connects with a de-isobutene column, wherein the de-isobutene column separates ETBE and removes isobutene by distillation and the removed isobutene is blended into the isobutene primary product.

15. The method as claimed in claim 13, wherein the second catalytic distillation column has at least a catalyst, where the catalyst is an ion exchange resin with sulfonic acid group, the ion exchange resin with sulfonic acid group having acid capacity more than 2.0 meq/g.

16. The method as claimed in claim 15, wherein the catalyst in the second catalytic distillation column is a zeolite or aluminum silicon oxide which is treated by fluoride, sulfuric acid, or sulfonic acid.

17. The method as claimed in claim 1, wherein before the step of feeding the TBA mixture into the rectification zone of the first catalytic distillation column, further comprises feeding the TBA mixture to an de-butanol column to separate TBA from other butanol isomers.

18. The method as claimed in claim 4, wherein the catalyst in the catalytic zone is a zeolite or aluminum silicon oxide which treated by fluoride, sulfuric acid, or sulfonic acid.

* * * * *